(12) United States Patent
Donhowe et al.

(10) Patent No.: US 9,517,000 B2
(45) Date of Patent: Dec. 13, 2016

(54) METHOD AND SYSTEM FOR STEERABLE MEDICAL DEVICE PATH DEFINITION AND FOLLOWING DURING INSERTION AND RETRACTION

(71) Applicant: Intuitive Surgical Operations, Inc., Sunnyvale, CA (US)

(72) Inventors: Caitlin Q. Donhowe, Sunnyvale, CA (US); Amir Belson, Los Altos, CA (US); Kristoffer J. Donhowe, Sunnyvale, CA (US); Kenneth R. Krieg, Fremont, CA (US); Eric M. Storne, Menlo Park, CA (US); Thomas J. Yorkey, San Ramon, CA (US); Jun Zhang, Union City, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 223 days.

(21) Appl. No.: 14/042,876

(22) Filed: Oct. 1, 2013

(65) Prior Publication Data

US 2014/0031625 A1    Jan. 30, 2014

Related U.S. Application Data

(60) Division of application No. 12/613,768, filed on Nov. 6, 2009, now Pat. No. 8,568,302, which is a
(Continued)

(51) Int. Cl.
*A61B 1/00* (2006.01)
*A61B 1/005* (2006.01)
*A61B 17/00* (2006.01)

(52) U.S. Cl.
CPC .......... *A61B 1/0051* (2013.01); *A61B 1/00009* (2013.01); *A61B 1/00147* (2013.01);
(Continued)

(58) Field of Classification Search
USPC ........ 600/103, 106, 114, 117, 118, 139, 141, 600/142, 145; 606/130, 139; 128/920
See application file for complete search history.

(56) References Cited

U.S. PATENT DOCUMENTS 6,468,203 B2   10/2002   Belson
6,610,007 B2    8/2003   Belson et al.
(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Thomas J Sweet
*Assistant Examiner* — Alexandra Newton

(57) ABSTRACT

Waypoints for a steerable medical device are stored as the steerable medical device is moved within a patient. The stored waypoints are an ordered sequence of locations. The ordered sequence of locations defines a safe path within the patient for moving an articulatable portion of the steerable medical device. The articulatable portion of the steerable medical device is constrained to follow the safe path as the articulatable portion moves within the patient. For example, the articulatable portion of the steerable medical device is constrained to remain within a boundary region enclosing the safe path as the articulatable portion of the steerable medical device follows the safe path.

6 Claims, 9 Drawing Sheets

Related U.S. Application Data continuation-in-part of application No. 12/613,739, filed on Nov. 6, 2009.

(60) Provisional application No. 61/113,534, filed on Nov. 11, 2008.

(52) U.S. Cl.
 CPC ......... *A61B 90/03* (2016.02); *A61B 2017/003* (2013.01); *A61B 2034/107* (2016.02)

(56) References Cited

U.S. PATENT DOCUMENTS

| | | |
|---|---|---|
| 8,568,302 B2 | 10/2013 | Donhowe et al. |
| 2003/0191367 A1 | 10/2003 | Belson et al. |
| 2004/0176683 A1 | 9/2004 | Whitin et al. |
| 2004/0249269 A1 | 12/2004 | Shiono et al. |
| 2006/0258912 A1 | 11/2006 | Belson et al. |
| 2007/0135803 A1 | 6/2007 | Belson |
| 2007/0197896 A1 | 8/2007 | Moll et al. |
| 2007/0249901 A1 | 10/2007 | Ohline et al. |
| 2007/0270650 A1 | 11/2007 | Eno et al. |
| 2008/0234700 A1 | 9/2008 | Trovato et al. |
| 2008/0287963 A1 | 11/2008 | Rogers et al. |
| 2009/0099420 A1 | 4/2009 | Woodley et al. |
| 2009/0137952 A1 | 5/2009 | Ramamurthy et al. |
| 2009/0171271 A1 | 7/2009 | Webster et al. |
| 2009/0216083 A1 | 8/2009 | Durant et al. |
| 2010/0121145 A1 | 5/2010 | Donhowe |
| 2010/0121148 A1 | 5/2010 | Donhowe et al. |
| 2010/0121151 A1 | 5/2010 | Donhowe et al. |

METHOD AND SYSTEM FOR STEERABLE MEDICAL DEVICE PATH DEFINITION AND FOLLOWING DURING INSERTION AND RETRACTION

RELATED APPLICATION

The present application is a divisional application of U.S. patent application Ser. No. 12/613,768 (filed Nov. 6 2009), which is a continuation-in-part application of commonly assigned U.S. patent application Ser. No. 12/613,739 (filed Nov. 6, 2009, disclosing "Method And System For Steerable Medical Device Path Definition And Following During Insertion And Retraction"), which claims the benefit of U.S. Provisional Patent Application No. 61/113,534 (filed Nov. 11, 2008 disclosing "Method for Robotic Endoscope Path Definition and Following During Insertion and Retraction"), each of which is incorporated herein by reference in its entirety.

BACKGROUND

Field of Invention

Aspects of this invention are related to medical device path planning, and more particularly are related to path planning for an articulatable multi-segment medical device.

Related Art

An endoscope is a medical device for visualizing the interior of a patient's body. Endoscopes have been used for a variety of medical diagnostic procedures and for a variety of medical interventional procedures.

Many different types of endoscopes are known. For example, one steerable endoscope has an elongated body with a steerable distal portion and an automatically controlled proximal portion. Such an endoscope is described in U.S. Pat. No. 6,468,203 B2, entitled "Steerable Endoscope and Improved Method of Insertion," of Amir Belson issued on Oct. 22, 2002, which is incorporated herein by reference in its entirety.

In general, conventional medical device path-planning is performed using medical imaging data usually CAT, X-ray, MRI, PET of fluoroscopy imaging data. Path-planning is considered in U.S. Pat. No. 5,611,025, entitled "Virtual internal cavity inspection system," issued Mar. 11, 1997; U.S. Pat. No. 7,167,180, entitled "Automatic path planning system and method," issued Jan. 23, 2007; U.S. Pat. No. 6,380,958, entitled "Medical-technical System," issued Apr. 30, 2002; U.S. Patent Application Publication No. US 2008/0091340 A1 (filed Dec. 26, 2004, disclosing "Targeted Marching"); and U.S. Patent Application Publication No. US 2003/0109780 A1 (filed Jun. 6, 2002, disclosing "Methods and Apparatus for Surgical Planning").

SUMMARY

Unlike prior art methods that required path planning prior to use of a steerable medical device, waypoints of a steerable medical device are stored as the device is moved within a patient. The stored waypoints are an ordered sequence of locations. The ordered sequence of locations defines a safe path within the patient for moving an articulatable portion of the steerable medical device.

Thus, the articulatable portion of the steerable medical device is constrained to follow the safe path as the articulatable portion moves within the patient or as the device is inserted into the patient. In one aspect, the articulatable portion of the steerable medical device is constrained to remain within a boundary region enclosing the safe path.

In one aspect, a process of constraining the steerable medical device includes retrieving, by a processor, the stored ordered sequence of locations. The processor next generates, using the ordered sequence of locations, a configuration of the articulatable portion of the steerable medical device so that the device follows the safe path. Based on the configuration, the processor sends at least one command to a controller to actuate the articulatable portion of the steerable medical device based on the configuration.

In one embodiment, the articulatable portion of the steerable medical device includes a segment of the steerable medical device. The segment, in turn, includes a plurality of links.

In another aspect, the boundary region is a tube having a cross-section. Examples of cross-sections include, but are not limited to, a circular cross-section, an oblate cross-section, and a rectangular cross-section.

In still yet another aspect, constraining the articulatable portion of the steerable medical device to remain within a boundary region enclosing the safe path includes generating position and orientation data for each of the plurality of segments. This process uses the ordered sequence of locations and a kinematic model of the plurality of segments of the steerable medical device.

The process of generating position and orientation data for each of the plurality of segments includes minimizing a cost function. In one aspect, minimizing a cost function further includes minimizing the sum of the absolute values of relative joint angles, with an additional constraint that link positions must remain within some distance of the safe path formed by the waypoints.

In another embodiment, a process maintains articulatable segments of a medical device within a boundary region while transmitting a proximal roll to the distal end of the device. This is done on a per segment basis, from a proximal end of each articulatable segment of the medical device to a distal end of the each articulatable segment. A shape of the each articulatable segment is maintained during the transmitting so that each articulatable segment remains in the boundary region.

In one aspect, the roll is transmitted segment by segment by generating a new pitch angle $\alpha'$ and a new yaw angle $\beta'$ for an articulatable segment while maintaining an approximate bend angle $\phi$ and a direction $\theta$ when a base of the articulatable segment rolls though an angle $-\Delta\gamma$. The articulatable segment prior to the roll had a pitch angle $\alpha$ and a yaw angle $\beta$. The approximate bend angle $\phi$ is $$\phi = \sqrt{\alpha^2 + \beta^2}.$$

The direction $\theta$ is $$\theta = \arctan(\alpha/\beta),$$

where arctan represents the arctangent function.

In another aspect, the roll is transmitted by performing an iterative solution on a processor using a kinematic model. The iterative solution is done on an articulatable segment by articulatable segment basis to generate orientation data corresponding to the desired distal roll for a given proximal roll for each articulatable segment. The orientation data includes pitch and yaw angles, in one aspect. The processor sends at least one command to a controller of the medical device to configure the medical device so that each articulatable segment has the yaw and pitch angles for that articulatable segment.

An apparatus includes a steerable medical device having an articulatable portion. The articulatable portion includes at least one articulatable segment. The apparatus also includes a controller, coupled to the steerable medical device. The controller includes a processor, and a medical device controller coupled to the processor and to the steerable medical device. The processor stores in the memory an ordered sequence of locations of waypoints. The processor also analyzes the ordered sequence of locations and outputs to the medical device controller at least one command to constrain the articulatable portion within a boundary region enclosing a safe path defined by the ordered sequence of location.

Figure 1:
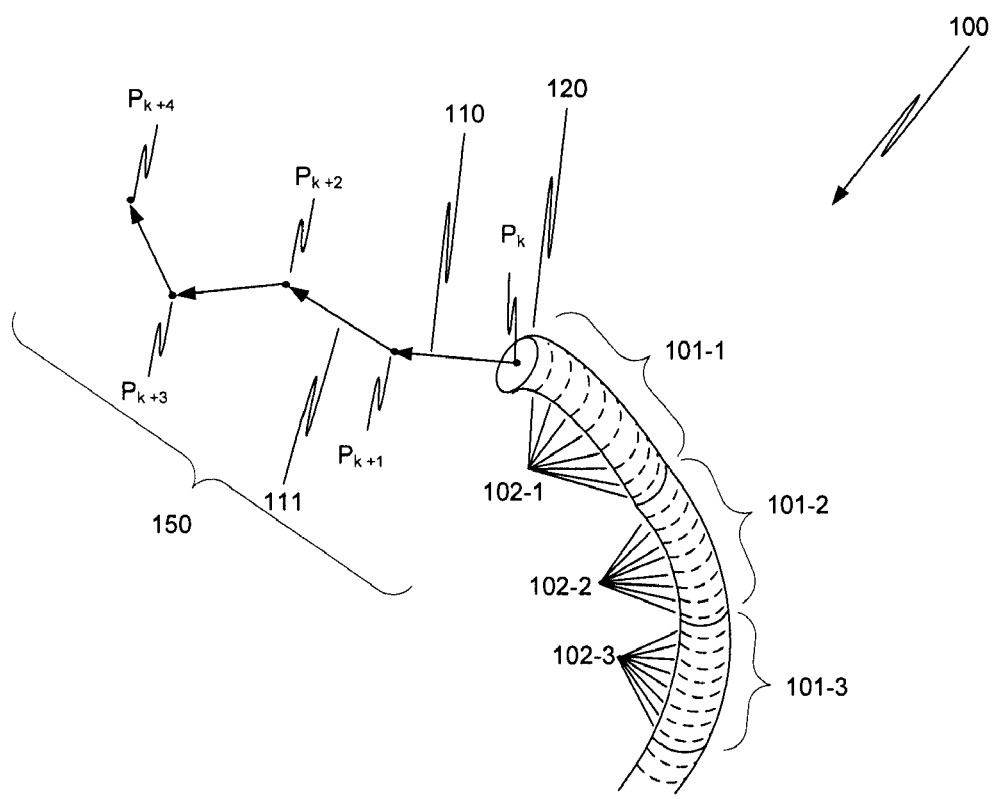
FIG. 1 is a diagrammatic view of a steerable medical device including an articulatable portion, and a safe path.

In the drawings, the first digit of a figure number indicates the figure in which the element with that figure number first appeared.

DETAILED DESCRIPTION

In one aspect, a steerable medical device 100 (FIG. 1), sometimes referred to as medical device 100, includes a plurality of segments 101-1, 101-2, 101-3 . . . . In the embodiment of FIG. 1, at least three segments 101-1, 101-2, 101-3 include a plurality of movable links 102-1, 102-2 and 102-3, respectively. In one aspect, a tip of steerable medical device 100 is at distal end 120 and typically includes at least a camera.

The use of a steerable medical device with at least three segments each having a plurality of movable links is illustrative only and in not intended to be limiting. In view of this disclosure, a steerable medical device may include from at least one segment having a plurality of links to a number of segments with movable links needed to provide the required functionality for the steerable medical device.

An example of a steerable medical device 100 is a steerable endoscope. In the following description, steerable medical device 100 is referred to as steerable endoscope 100. The use of steerable endoscope 100 as an example of a steerable medical device is illustrative only and is not intended to be limiting to this specific steerable medical device. An example of a steerable endoscope suitable for use in this disclosure is described in commonly assigned, U.S. Patent Application Publication No. 2007/0249901 A1 (filed Mar. 28, 2006; disclosing "Instrument Having Radio Frequency Identification Systems and Methods for Use."), which is incorporated herein by reference in its entirety.

The plurality of movable links in a segment allows that segment to be articulated as steerable endoscope 100 moves into and out of a patient. Thus, such segments are referred to as articulatable segments.

In one aspect, an operator manipulates a direction controller 245 (FIG. 2) to move the tip of steerable endoscope 100 in a particular direction within the patient. In response to commands from a processor in processor module 250, as described more completely below, and a signal from direction controller 245, an endoscope controller 240 (FIG. 2) for steerable endoscope 100 configures each of the links so that each segment is constrained to move along, e.g., to follow, a known safe path 150 (FIG. 1) that is defined, in one aspect, by movement of the tip of endoscope 100.

In one embodiment, as the operator steers the tip of steerable endoscope 100 through the patient, a safe path is generated. More specifically, as the operator inserts steerable endoscope 100 into a patient and moves steerable endoscope 100 towards a desired location, an ordered sequence of locations $\{P_k, P_{k+1}, P_{k+2}, P_{k+3}, P_{k+4}\}$ (FIG. 1) of the tip of endoscope 100 are recorded in a memory 230 (FIG. 2) as waypoint data 231, in this example.

The ordered sequence of locations $\{P_k, P_{k+1}, P_{k+2}, P_{K+3}, P_{k+4}\}$ (FIG. 1) represent the motion of the tip of steerable endoscope 100 through the patient. Thus, the ordered sequence of locations $\{P_k, P_{k+1}, P_{k+2}, P_{k+3}, P_{k+4}\}$ represent a safe path 150, which has been chosen by the operator, for steerable endoscope 100 to follow as steerable endoscope 100 is inserted into and withdrawn from the patient.

Using the tip movement to generate an ordered sequence of locations that define safe path 150 is illustrative only and is not intended to be limiting. Alternatively, steerable endoscope 100 could be inserted in a passive state, and then all the inserted articulatable segments activated at one. The positions of the links in the articulatable segments at the time of activation provide an ordered sequence of locations that define safe path 150 for additional insertion and for retraction of steerable endoscope 100.

In one aspect, as described more completely below, all trailing segments 101-1, 101-2, 101-03 . . . of steerable endoscope 100 are constrained to follow safe path 150 that is defined by ordered sequence of locations $\{P_k, P_{k+1}, P_{k+2}, P_{k+3}, P_{k+4}\}$. However, trailing segments 101-1, 101-2, 101-03 . . . may not follow safe path 150 exactly. In one aspect, the operator can define a boundary region around safe path 150. The boundary region (See FIGS. 3A to 3C) is a volume inside which steerable endoscope 100 can move safely. In one aspect, all trailing segments 101-1, 101-2, 101-03 . . . are constrained to remain within this boundary region as steerable endoscope 100 moves into the patient.

Also, in another aspect, as medical device 100 is withdrawn from the patient, articulatable segments 101-1, 101-2, 101-03 . . . are constrained to remain within this boundary region. Hence, unlike prior art techniques that required advance planning, a safe route for medical device 100 into and out of a patient is generated based on waypoint data 231 recorded as steerable endoscope 100 moves into the patient.

When segment 101-1 is considered a trailing segment, as just described, segment 101-1 is controlled in the same way as the other trailing articulatable segments. However, in another insertion mode, segment 101-1 remains directly controlled by the operator and does not change shape with insertion. In this insertion mode, segment 101-1 would not be considered a trailing segment.

Figure 3A:
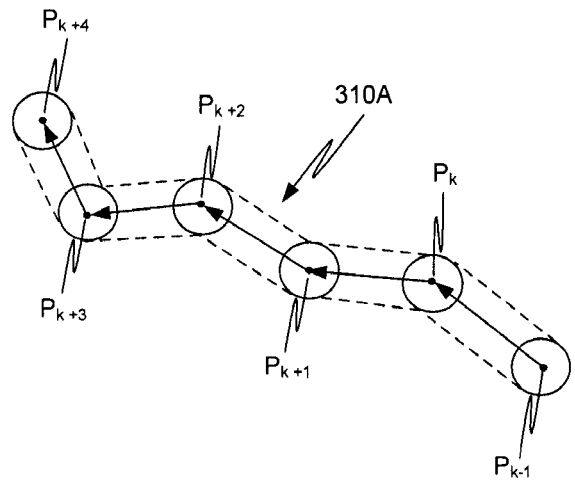
FIGS. 3A to 3C are diagrammatic views of boundary regions enclosing a safe path.
Figure 3B:
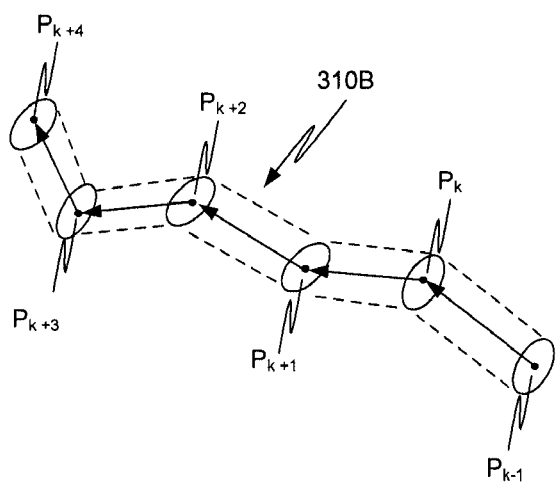
Figure 3C:
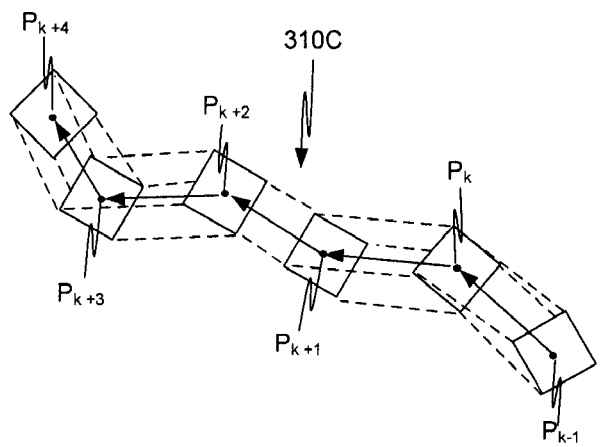

FIGS. 3A to 3C are illustrations of boundary regions 310A to 310C, with different cross-sectional shapes, for safe path 150 defined by ordered sequence of locations $\{P_k, P_{k+1}, P_{k+2}, P_{k+3}, P_{k+4}\}$. In FIG. 3A, boundary region 310A has a circular cross-section. In FIG. 3B, boundary region 310B has an oblate cross-section. In FIG. 3C, boundary region 310C has a rectangular cross-section, and in particular, a specific instance of a rectangular cross-section, a square cross-section.

In one aspect, each location $P_k$ is a point in space ($x_k$, $y_k$, $z_k$) relative to a fixed reference frame. Thus, each of boundary regions 310A, 310B, 310C defines a three-dimensional volume enclosing safe path 150. This volume is referred to as a tube having a cross section to convey the three-dimensional characteristics of the volume. Tube, as used here, is not a physical tube inserted in the patient to define the volume.

The particular cross-sectional shapes of the boundary regions illustrated in FIGS. 3A to 3C are illustrative only and are not intended to be limiting. In view of this disclosure, for a particular medical procedure and steerable medical device, an appropriately shaped boundary region or regions can be selected.

It is not necessary that the boundary region have the same cross-sectional shape over the entire extent of the safe path. For example, a first portion of a boundary region could have a first cross-sectional shape, and a second portion of the boundary region could have a second cross-sectional shape that is different from the first cross-sectional shape.

Figure 4:
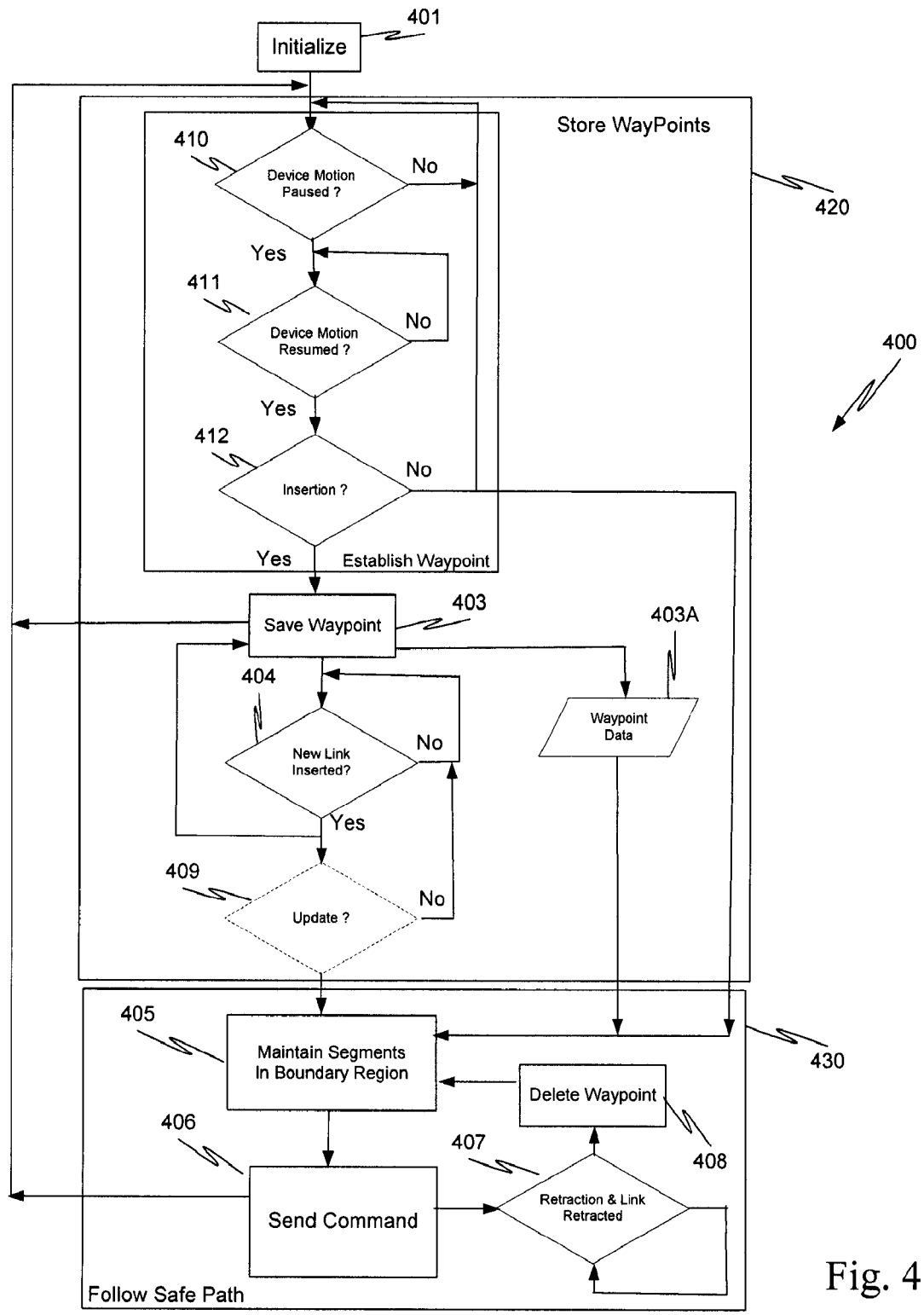
FIG. 4 is a process flow diagram for one embodiment of a method of configuring a steerable medical device to follow a safe path.

FIG. 4 is a process flow diagram for one embodiment of a method 400 used with a steerable medical device such as steerable endoscope 100. In one aspect, instructions in a METHOD 400 module 232 (FIG. 2) in memory 230 are executed on a processor in processor module 250 to perform at least some of the operations described more completely below.

In method 400, STORE WAYPOINTS operation 420, as described more completely below, saves waypoints of the tip of steerable endoscope 100 as an ordered sequence of locations. The ordered sequence of locations represents the trajectory of the tip as steerable endoscope 100 is inserted into the patient. As described above, the ordered sequence of locations defines a safe path 150 that has been selected by the operator of steerable endoscope 100.

The stored ordered sequence of locations is retrieved and analyzed in FOLLOW SAFE PATH process 430. FOLLOW SAFE PATH process 430 configures the articulatable portion of endoscope 100 so that the articulatable portion of endoscope 100 is constrained to follow safe path 150 as the articulatable portion moves within the patient. Herein, following the safe path does not mean that the safe path is followed exactly, but rather that the articulatable portion steerable endoscope 100 stays at least within a safe region, sometimes called a boundary region, about safe path 150.

In FIG. 4, one embodiment of STORE WAYPOINTS operation 420 and FOLLOW SAFE PATH process 430 are illustrated and described more completely below. This embodiment is illustrative only and is not intended to be limiting to the specific operations and processes described. In view of this disclosure, one knowledgeable in the field can utilize other techniques to move the articulatable portion of a steerable medical into and out of a patient while following the safe path described herein.

In FIG. 4, upon initiation of method 400, an INITIALIZE operation 401 is performed. INITIALIZE operation 401 initializes any variables, memory structures etc. that are need for subsequent operations in method 400. In one aspect, INITIALIZE operation 401 uses display controller 235 (FIG. 2) to generate a display on display device 210 that permits the operator of steerable endoscope 100 to select parameters that define the extent of the boundary region, for example. Upon completion INITIALIZE operation 401 (FIG. 4) transfers processing to ESTABLISH WAYPOINT operation 402 in STORE WAYPOINTS operation 420.

In ESTABLISH WAYPOINT operation 402, a waypoint on the safe path of the endoscope is established. This can be done in a variety of ways. Accordingly, check operations 410 to 412, as discussed more completely below, are illustrative only and are not intended to be limiting to this particular implementation.

In one aspect, as the operator inserts steerable endoscope 100 into a body cavity (for instance, through an incision in the stomach into the abdominal cavity) insertion is paused periodically. When motion of endoscope 100 is paused, DEVICE MOTION PAUSED check operation 410 transfers processing to DEVICE MOTION RESUMED check operation 411.

If steerable endoscope 100 is paused to determine a safe trajectory for the tip, the operator uses the camera and illumination at the tip of steerable endoscope 100 to determine a safe trajectory inside the body cavity. When viewing the interior of the body cavity and determining a safe direction for farther insertion, the endoscope tip may be oriented in any direction to provide views of the body cavity.

Once a safe trajectory is determined, the tip is oriented in the direction that the operator intends steerable endoscope 100 to travel upon farther insertion. The operator then inserts endoscope 100 farther into the patient. However, the operator could also retract endoscope 100 after the pause. Thus, upon resumption of motion of endoscope 100, DEVICE MOTION RESUMED check operation 411 transfers processing to INSERTION check operation 412.

INSERTION check operation 412 determines whether after the pause, the operation is continuing to insert endoscope 100 or is retracting endoscope 100. If the operator is continuing to insert endoscope 100, check operation 412 transfers processing to SAVE WAYPOINT operation 403. Conversely, if the operator is retracting endoscope 100, check operation 412 transfers to DEVICE MOTION PAUSED check operation 410 and to MAINTAIN SEGMENTS IN BOUNDARY REGION operation 405.

Again, the combination of operations 410 to 412 is one way to allow an operator to establish a waypoint. Alternatively, the operator could, for example, push a button when a safe trajectory has been identified and the operator is about to move the endoscope tip on that trajectory.

Figure 2:
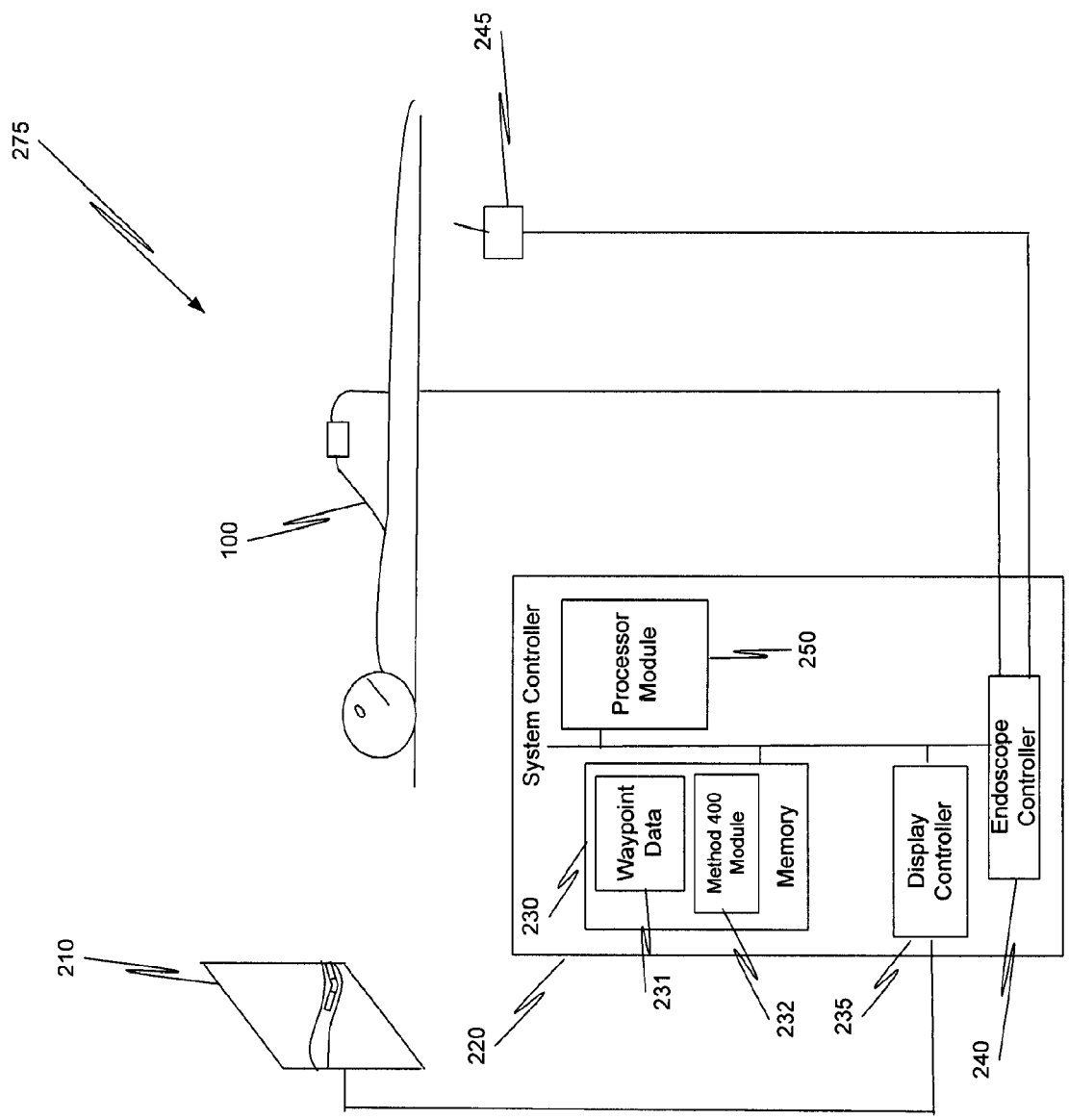
FIG. 2 is a diagrammatic view of an apparatus used in one aspect of the processes and operations described herein.

SAVE WAYPOINT operation 403 records the previous location of the tip as a waypoint in WAYPOINT DATA 403A, which in FIG. 2 is shown as waypoint data 231. SAVE WAYPOINT operation 403, upon completion, transfers processing to NEW LINK INSERTED check operation 404. SAVE WAYPONT operation 403 also transfers back to the start of ESTABLISH WAYPOINT operation 402 in case the operator decides to change the direction of the safe trajectory.

In this example, insertion of a link is used as a trigger to record another waypoint for the tip. However, other criteria can be used so long as locations of the tip are saved with sufficient resolution to permit determining a safe path. As steerable endoscope 100 is moved further into the patient along the safe trajectory, as each new link is inserted in the patient, the location of the tip is saved as another waypoint. One way of determining when a link is inserted in described in commonly assigned U.S. patent application Ser. No.

12/613,698, entitled "METHOD AND SYSTEM FOR MEASURING INSERTED LENGTH OF A MEDICAL DEVICE USING INTERNAL REFERENCED SENSORS" of Caitlin Donhowe, filed on Nov. 6, 2009, which is incorporated herein by reference in its entirety. Another way of determining when a link is inserted is to use an external position sensor. In this example, when a new link is inserted, NEW LINK INSERTED check operation 404 transfers processing to SAVE WAYPOINT operation 403, which was described above, and to UPDATE check operation 409.

UPDATE check operation 409 is shown with a dotted line in FIG. 4 because check operation 409 is optional. In one aspect, the configuration of the trailing segments of endoscope 100 is updated only after a predefined number of new waypoints have been saved. In this aspect, UPDATE check operation 409 does not transfer processing to process 405 until the predefined number of new waypoints is available in WAYPOINT DATA 403A. Also, UPDATE check operation 409 checks the states of the articulatable segments and if none of the articulatable segments have state articulating, UPDATE check operation 409 does not transfer processing to process 405. Alternatively, the configuration of the trailing segments of endoscope 100 is updated for each new waypoint and so UPDATE check operation 409 is not needed.

In this embodiment, FOLLOW SAFE PATH process 430 includes MAINTAIN SEGMENTS IN BOUNDARY REGION process 405 and SEND COMMAND process 406. MAINTAIN SEGMENTS IN BOUNDARY REGION process 405 uses the saved waypoints to generate a configuration for each of the inserted links so that trailing segments 101-1 to 101-3 follow safe path 150 of the tip as defined by the waypoints. As noted above, for some steerable medical devices, it may not be possible to configure the trailing segments to follow exactly safe path 150. Thus, in one aspect, a boundary region about the ordered sequence of locations $\{P_k\}_{k=1}^N$ is generated. Here, $P_k$ denotes the Cartesian coordinates of the endoscope tip when the number of the inserted links is k. After the endoscope has been inserted for N links, the path trajectory of the endoscope tip is recorded as ordered sequence of locations $\{P_k\}_{k=1}^N$ in memory 230 (FIG. 2).

As described above, the boundary region defines a volume around safe path 150, i.e., a volume that encloses safe path 150. The trailing segments can safely pass through any part of the boundary region as the trailing segments move towards the surgical site, or move away from the surgical site.

Figure 5:
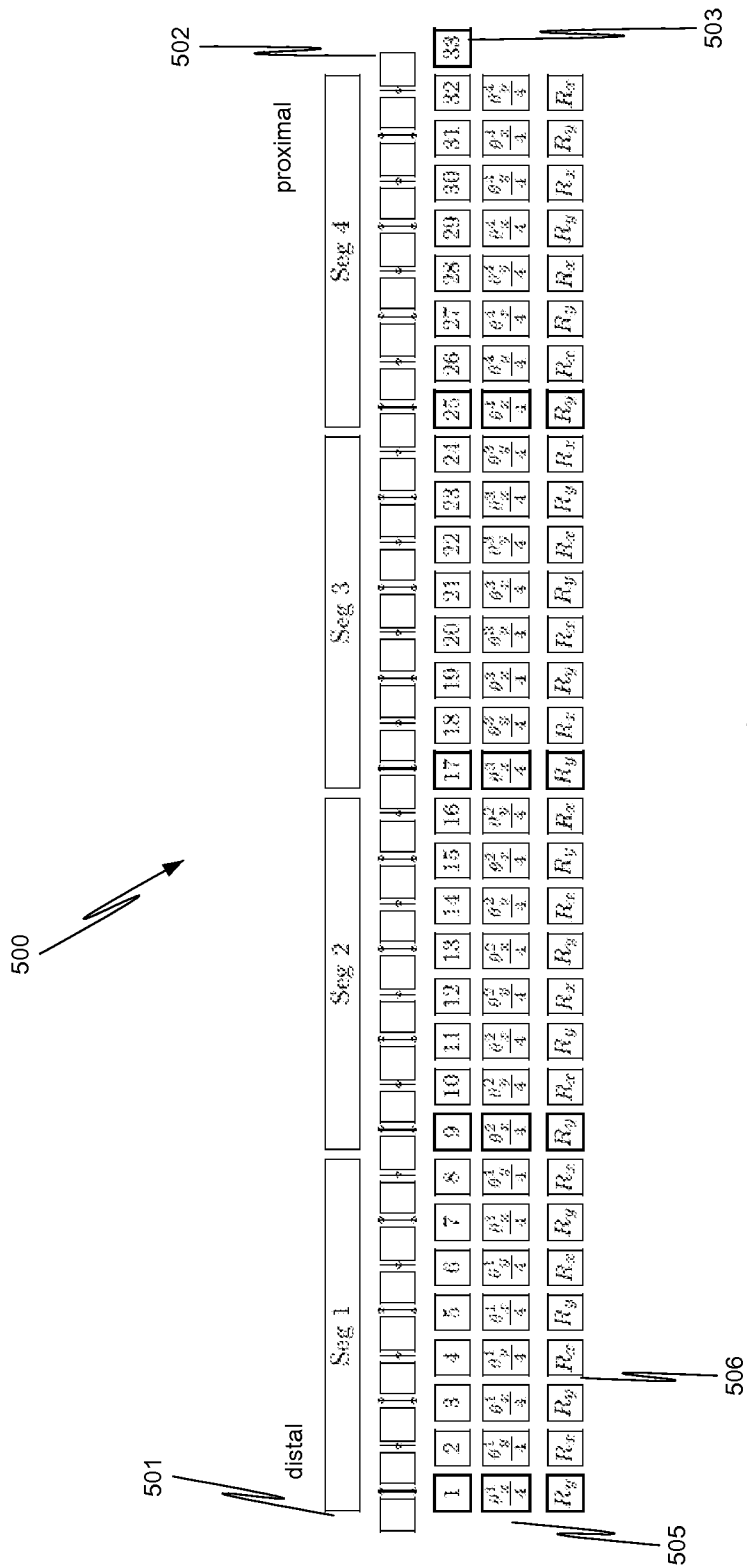
FIG. 5 is a diagrammatic view of elements of a kinematic model that can be used in the method of FIG. 4.

In one aspect, a kinematic model of steerable endoscope 100, such as model 500 in FIG. 5, is used in MAINTAIN SEGMENTS IN BOUNDARY REGION process 405. In kinematic model 500, (FIG. 5), a first level 501 of model 500 defines the number of articulatable segments in a plurality of articulatable segments of the steerable endoscope. In this example, the steerable endoscope has four articulatable segments Seg 1, Seg 2, Seg 3, and Seg 4.

A second level 502 of model 500 is a representation of links and joints in each of four articulatable segments Seg 1, Seg 2, Seg 3, and Seg 4. In this example, each segment includes eight links, where adjacent links are separated by a joint. The joints are numbered sequentially from the distal end to the proximal end of the endoscope, starting with a value one as shown in a third level 503 of model 500. (This numbering sequence is for convenience only. In other aspects, the numbering may increase in going from a proximal location towards a distal location.) Each link has a fixed length and the associated joint can rotate in a single plane, either the x-plane or the y-plane. The joints alternate so adjacent links rotate in different planes.

In model 500, each of four articulatable segments Seg 1, Seg 2, Seg 3, and Seg 4 has an angle of rotation about the x-axis and an angle of rotation about the y-axis. For articulatable segment Seg 1, the angle of rotation about the x-axis is $\theta_y^1$, (sometimes referred to as pitch) and the angle of rotation about the y-axis is $\theta_x^1$ (sometimes referred to as yaw). For articulatable segment Seg 2, the angle of rotation about the x-axis is $\theta_y^2$, and the angle of rotation about the y-axis is $\theta_x^2$. For articulatable segment Seg 3, the angle of rotation about the x-axis is $\theta_y^3$, and the angle of rotation about the y-axis is $\theta_x^3$. For articulatable segment Seg 4, the angle of rotation about the x-axis is $\theta_y^4$, and the angle of rotation about the y-axis is $\theta_x^4$.

Row 505 in model 500 gives the initial constraint on the joint angles. In this example, the joint angles for a segment are assumed to be equal. Thus, each joint angle is one-fourth of the corresponding segment angle. Row 506 in model 500 gives the roll matrix for each joint.

In this model, y-links are links that cause motion in the y-direction rather than links that rotate about the y-direction. This definition results in $R_x(\theta_y)$. Similarly, in this model, x-links are links that cause motion in the x-direction rather than links that rotate about the x-direction. This definition results in $R_y(\theta_x)$ Those knowledgeable in the field understand that alternative definitions can be used in the kinematic model, where x-links are links that rotate about the x-direction and y-links are links that rotate about the y-direction. Irrespective of the kinematic model definitions, the results are equivalent.

Thus, model 500 is illustrative only and is not intended to be limiting. Model 500 is used in one example that is developed more completely below.

Using stored ordered sequence of locations $\{P_k\}_{k=1}^N$ and kinematic model 500, a cost function is minimized to generate position and orientation data of the endoscope segments in MAINTAIN SEGMENTS IN BOUNDARY REGION process 405. Specifically, in one aspect, positions and orientations are generated for each of the links in the articulatable portion of endoscope 100. The positions and orientations are constrained within the boundary region.

The cost function allows the position and orientation to be optimized for a variety of criteria, for example, but not limited to: 1) maximum tip controllability; 2) maximum distance of the segments from inverse-kinematic singularities; 3) maximum distance of the segments from articulation limits; 4) maximum distance from user-defined body-cavity boundaries (organs, adhesions, etc.); 5) minimum distance from the defined path.

In process 405, the cost function may be a dynamically changing function of any number of criteria. However, the number of criteria is selected so the cost function can be minimized and the segments positioned to achieve the constrained movement within an endoscope movement time acceptable to the operator. Conventional techniques are used by a processor to minimize the cost function selected subject to the position constraints imposed.

In an additional aspect, an embodiment of process 405 determines the optimal configuration of the segments (relative segment angles) to satisfy the constraint that the segment links stay "near to" the path defined by the tip forward motion and any additional constraints on the link (or segment) positions.

For example, in process 405, the segments may be allowed to assume positions within a tubular bounding region 310A (FIG. 3A) around the tip path while encouraging tip manipulability. One way to encourage tip manipulability in process 405 is to minimize the sum of the absolute values of the relative joint angles, with the additional constraint that the link positions not deviate by more than a distance Δ at each of the waypoints in ordered sequence of locations $\{P_k\}_{k=1}^{N}$. In one aspect, distance Δ is specified by the operator.

Upon determining the configuration for each of the articulatable segments, MAINTAIN SEGMENTS IN BOUNDARY REGION process 405 transfers processing to SEND COMMAND process 406 (FIG. 4). In SEND COMMAND process 406, the processor in processor module 250 (FIG. 2) sends at least one command to the motors in endoscope controller 240 to configure the articulatable segments based on the locations and orientations generated in process 405, i.e., based on the configuration generated in process 405. This constrains the articulatable segments within the boundary region as endoscope 100 moves further into the patient.

SEND COMMAND process 406 transfers to DEVICE MOTION PAUSED check operation 410 and to RETRACTION AND LINK RETRACTED check operation 407. RETRACTION AND LINK RETRACTED check operation 407 determines whether endoscope 100 is being retracted and whether a link has been retracted. If both of these conditions are true, check operation 407 transfers to DELETE WAYPOINT operation 408.

DELETE WAYPOINT operation 408 deletes the stored waypoint for the withdrawn link and transfers to operation 405. Hence, operations 405 to 408 cause endoscope 100 to follow safe path 150 as endoscope 100 is retracted from the patient.

In the example of FIG. 2, in response to the command, endoscope controller 240 configures the segments so that as the segments move forward, the segments are constrained to stay within the boundary region. Thus, the segments may not follow the trajectory of the tip exactly, but the segments follow a path within the boundary region that is safe.

When the operator starts to withdraw the endoscope from the patient, the waypoints in the stored ordered sequence of locations $\{P_k\}_{k=1}^{N}$ decrease by one as each link is withdrawn. Processes 405 and 406 are used as steerable endoscope is withdrawn to maintain endoscope 100 with the boundary region.

As a further example of process 405, the control of the joint angles at constant endoscopic length increments is considered such that the endoscope configuration is kept within a safety area, the boundary region described above, during the process of insertion and withdrawal. In this example, a configuration of the trailing links that is closest, as measured by Euclidean norm, to the tip trajectory is generated in process 405, since the tip trajectory represents a safe route selected by the operator.

As described above $P_k$ denotes the Cartesian coordinate of the endoscope tip when the number of the inserted links is k. After the endoscope has been inserted for N links, the path trajectory of the endoscope tip is recorded in a series $\{P_k\}_{k=1}^{N}$. Process 405 controls the joint angles to achieve an endoscope link configuration close to the waypoints in recorded series $\{P_k\}_{k=1}^{N}$. This is formulated as the following optimization, where J is the cost function discussed above:

$$\min_{\theta} J = \frac{1}{2}\sum_{k=1}^{N} \|p_k - P_k\|^2 \tag{1}$$

subject to $$\theta_{min} \leq \theta \leq \theta_{max}, \tag{2}$$

where $p_k$ is the coordinate of each link determined by the kinematics model.

To apply an iterative procedure to solve this problem, assume that at the n-th step, a solution is $\theta_n$ and the next increment $\Delta\theta_n$ is to be determined. The new link coordinate is approximated by $$p^{n+1} \approx p^n + \nabla_{\theta_n} p \cdot \Delta\theta_n. \tag{3}$$

Substituting expression (3) into the cost function gives:

$$J^{n+1} = \frac{1}{2}\|p^{n+1} - P\|^2 \approx \frac{1}{2}\|\nabla_{\theta_n} p \cdot \Delta\theta_n + p^n - P\|^2. \tag{4}$$

This is indeed a quadratic programming problem:

$$\min_{\Delta\theta} J = \frac{1}{2}\Delta\theta_n (\nabla_{\theta_n} p)^T \nabla_{\theta_n} p \Delta\theta_n + (p^n - p)^T \nabla_{\theta_n} p \Delta\theta_n, \tag{5}$$

subject to $$\theta_{min} - \theta_n \leq \Delta\theta_n \leq \theta_{max} - \theta_n. \tag{6}$$

Kinematics Model

With respect to FIG. 5, let the first input parameter be defined as:

$$q = \begin{bmatrix} \theta_x^1 & \theta_y^1 \\ \theta_x^2 & \theta_y^2 \\ \theta_x^3 & \theta_y^3 \\ \theta_x^4 & \theta_y^4 \end{bmatrix}. \tag{7}$$

The vector of joint angles is defined as:

$$q_{jw} = \left[\frac{\theta_x^1}{4}, \frac{\theta_y^1}{4}, \frac{\theta_x^1}{4}, \frac{\theta_y^1}{4}, \frac{\theta_x^1}{4}, \frac{\theta_y^1}{4}, \frac{\theta_x^1}{4}, \frac{\theta_y^1}{4}, \frac{\theta_x^2}{4}, \right. \tag{8}$$

$$\frac{\theta_y^2}{4}, \frac{\theta_x^2}{4}, \frac{\theta_y^2}{4}, \frac{\theta_x^2}{4}, \frac{\theta_y^2}{4}, \frac{\theta_x^2}{4}, \frac{\theta_y^2}{4}, \frac{\theta_x^3}{4}, \frac{\theta_y^3}{4}, \frac{\theta_x^3}{4}, \frac{\theta_y^3}{4}, \frac{\theta_x^3}{4},$$

$$\left. \frac{\theta_y^3}{4}, \frac{\theta_x^3}{4}, \frac{\theta_x^4}{4}, \frac{\theta_y^4}{4}, \frac{\theta_x^4}{4}, \frac{\theta_y^4}{4}, \frac{\theta_x^4}{4}, \frac{\theta_y^4}{4}, \frac{\theta_x^4}{4}, \frac{\theta_y^4}{4}\right],$$

and the state of each link is defined as:

$$T_{1w}(1) = \begin{bmatrix} R_y\left(-\frac{\theta_x^1}{4}\right) & \begin{pmatrix} 0 \\ 0 \\ -a(1) \end{pmatrix} \\ 0 & 1 \end{bmatrix}, \tag{9}$$

$$T_{1w}(3) = \begin{bmatrix} R_y\left(-\frac{\theta_x^1}{4}\right) & \begin{pmatrix} 0 \\ 0 \\ -a(3) \end{pmatrix} \\ 0 & 1 \end{bmatrix},$$

$$T_{1w}(5) = \begin{bmatrix} R_y\left(-\frac{\theta_x^1}{4}\right) & \begin{pmatrix} 0 \\ 0 \\ -a(5) \end{pmatrix} \\ 0 & 1 \end{bmatrix},$$

$$T_{1w}(7) = \begin{bmatrix} R_y\left(-\frac{\theta_x^1}{4}\right) & \begin{pmatrix} 0 \\ 0 \\ -a(7) \end{pmatrix} \\ 0 & 1 \end{bmatrix},$$

$$T_{1w}(2) = \begin{bmatrix} R_x\left(\frac{\theta_y^1}{4}\right) & \begin{pmatrix} 0 \\ 0 \\ -a(2) \end{pmatrix} \\ 0 & 1 \end{bmatrix},$$

$$T_{1w}(4) = \begin{bmatrix} R_x\left(\frac{\theta_y^1}{4}\right) & \begin{pmatrix} 0 \\ 0 \\ -a(4) \end{pmatrix} \\ 0 & 1 \end{bmatrix},$$

$$T_{1w}(6) = \begin{bmatrix} R_x\left(\frac{\theta_y^1}{4}\right) & \begin{pmatrix} 0 \\ 0 \\ -a(6) \end{pmatrix} \\ 0 & 1 \end{bmatrix},$$

$$T_{1w}(8) = \begin{bmatrix} R_x\left(\frac{\theta_y^1}{4}\right) & \begin{pmatrix} 0 \\ 0 \\ -a(8) \end{pmatrix} \\ 0 & 1 \end{bmatrix},$$

where $$R_x(\theta) = \begin{bmatrix} 1 & 0 & 0 \\ 0 & \cos(\theta) & -\sin(\theta) \\ 0 & \sin(\theta) & \cos(\theta) \end{bmatrix}$$

and $$R_y(-\theta) = \begin{bmatrix} \cos(\theta) & 0 & -\sin(\theta) \\ 0 & 1 & 0 \\ \sin(\theta) & 0 & \cos(\theta) \end{bmatrix}.$$

The rest of the $T_{lw}$'s can be obtained in a similar fashion. In particular, $$T_{1w}(33) = \begin{bmatrix} I & \begin{pmatrix} 0 \\ 0 \\ -a(33) \end{pmatrix} \\ 0 & 1 \end{bmatrix}. \tag{10}$$

Notice that all these $T_{lw}$'s are in the Special Euclidean Lie group SE(4).

The cumulative transform to the base from the distal end of link k can be derived as $$T_{cl}(k) = \prod_{j=1}^{k} T_{1w}(j) = T_{1w}(1) \times T_{1w}(2) \times \ldots \times T_{1w}(k). \tag{11}$$

In this section, gradient $\nabla_\theta l_k$ is derived, where l is the position vector for link k. To this end, define the basis for the skew-symmetric matrix so(3) as follows:

$$\sigma_x = \begin{bmatrix} 0 & 0 & 0 \\ 0 & 0 & -1 \\ 0 & 1 & 0 \end{bmatrix}, \tag{12}$$

$$\sigma_y = \begin{bmatrix} 0 & 0 & 1 \\ 0 & 0 & 0 \\ -1 & 0 & 0 \end{bmatrix},$$

$$\sigma_z = \begin{bmatrix} 0 & -1 & 0 \\ 1 & 0 & 0 \\ 0 & 0 & 0 \end{bmatrix}.$$

The rotation matrices can then be described as $$R_x(\theta) = \exp(\sigma_x \theta),\ R_y(\theta) = \exp(\sigma_y \theta),\ R_z(\theta) = \exp(\sigma_z \theta). \tag{13}$$

Suppose that R is a rotation matrix $$R = \begin{bmatrix} r_{11} & r_{12} & r_{13} \\ r_{21} & r_{22} & r_{23} \\ r_{31} & r_{32} & r_{33} \end{bmatrix}. \tag{14}$$

Since $RR^T = I$, an important property for R can be derived:

$$R\sigma_x R^T = r_{11}\sigma_x + r_{21}\sigma_y + r_{31}\sigma_z, \tag{15}$$

$$R^T \sigma_x R = r_{11}\sigma_x + r_{12}\sigma_y + r_{13}\sigma_z, \tag{16}$$

$$R\sigma_y R^T = r_{12}\sigma_x + r_{22}\sigma_y + r_{32}\sigma_z, \tag{17}$$

$$R^T \sigma_y R = r_{21}\sigma_x + r_{22}\sigma_y + r_{23}\sigma_z. \tag{18}$$

Now, the gradient $dT_{cl}(k)/d\theta$ is derived. Let $$T_{1w}(k) = \begin{bmatrix} R_k & a_k \\ 0 & 1 \end{bmatrix} \tag{19}$$

and $$T_{cl}(k) = \begin{bmatrix} S_k & 1_k \\ 0 & 1 \end{bmatrix}.$$

It is easy to derive that $$S_k = R_1 R_2 \ldots R_k, \tag{20}$$

$$1_k = R_1 R_2 \ldots R_{k-1}a_k + R_1 R_2 \ldots R_{k-2}a_{k-1} + \ldots + R_1 a_2 + a_1 \tag{21}$$
$$= S_{k-1}a_k + S_{k-2}a_{k-1} + \ldots + S_1 a_2 + a_1,$$

and $l_1 = a_1$. We therefore have $$\frac{dS_k}{d\theta} = \frac{d}{d\theta}(R_1 R_2 \ldots R_k), \tag{22}$$

$$\frac{d1_k}{d\theta} = \frac{dS_{k-1}}{d\theta}a_k + \frac{dS_{k-2}}{d\theta}a_{k-1} + \ldots + \frac{dS_1}{d\theta}a_2,\ (k \geq 2). \tag{23}$$

When $\theta = \theta_x^1$, for $k \geq 7$, we have $$\frac{dS_k}{d\theta_x^1}S_k^T = \frac{d}{d\theta_x^1}(R_1 R_2 \ldots R_k)S_k^T \tag{24}$$

-continued $$= \frac{dR_1}{d\theta_x^1}(R_2 \ldots R_k)S_k^T + R_1R_2\frac{dR_3}{d\theta_x^1}(R_4 \ldots R_k)S_k^T +$$

$$R_1R_2R_3R_4\frac{dR_5}{d\theta_x^1}(R_6 \ldots R_k)S_k^T + R_1R_2R_3R_4R_5R_6\frac{dR_7}{d\theta_x^1}$$

$$(R_8 \ldots R_k)S_k^T$$

$$= \left(-\frac{\sigma_y}{4}\right) + R_1R_2\left(-\frac{\sigma_y}{4}\right)(R_1R_2)^T + \quad (25)$$

$$R_1R_2R_3R_4\left(-\frac{\sigma_y}{4}\right)(R_1R_2R_3R_4)^T + R_1R_2R_3R_4R_5R_6$$

$$\left(-\frac{\sigma_y}{4}\right)(R_1R_2R_3R_4R_5R_6)^T$$

$$= -\frac{\sigma_y}{4} + S_2\left(-\frac{\sigma_y}{4}\right)S_2^T + S_4\left(-\frac{\sigma_y}{4}\right)S_4^T + S_6\left(-\frac{\sigma_y}{4}\right)S_6^T, \quad (26)$$

which in turn yields $$\frac{dS_k}{d\theta_x^1} = -\frac{1}{4}(\sigma_y + S_2\sigma_yS_2^T + S_4\sigma_yS_4^T + S_6\sigma_yS_6^T)S_k. \quad (27)$$

For k=5 or 6, we obtain $$\frac{dS_k}{d\theta_x^1}S_k^T = -\frac{\sigma_y}{4} + S_2\left(-\frac{\sigma_y}{4}\right)S_2^T + S_4\left(-\frac{\sigma_y}{4}\right)S_4^T, \quad (28)$$

thus $$\frac{dS_k}{d\theta_x^1} = -\frac{1}{4}(\sigma_y + S_2\sigma_yS_2^T + S_4\sigma_yS_4^T)S_k;$$

for k = 3 or 4, $\quad (29)$ $$\frac{dS_k}{d\theta_x^1} = -\frac{1}{4}(\sigma_y + S_2\sigma_yS_2^T)S_k;$$

and for k = 1 or 2, $\quad (30)$ $$\frac{dS_k}{d\theta_x^1} = -\frac{1}{4}\sigma_yS_k;$$

In summary, $$\frac{dS_k}{d\theta_x^1} = \begin{cases} -\frac{1}{4}\sigma_yS_k, & k = 1, 2; \\ -\frac{1}{4}(\sigma_y + S_2\sigma_yS_2^T)S_k, & k = 3, 4; \\ -\frac{1}{4}(\sigma_y + S_2\sigma_yS_2^T + S_4\sigma_yS_4^T)S_k, & k = 5, 6; \\ -\frac{1}{4}(\sigma_y + S_2\sigma_yS_2^T + S_4\sigma_yS_4^T + S_6\sigma_yS_6^T)S_k, & k \geq 7. \end{cases} \quad (31)$$

$$\frac{dS_k}{d\theta_x^2} = \quad (32)$$

$$\begin{cases} 0, & k \leq 8; \\ -\frac{1}{4}(S_8\sigma_yS_8^T)S_k, & k = 9, 10; \\ -\frac{1}{4}(S_8\sigma_yS_8^T + S_{10}\sigma_yS_{10}^T)S_k, & k = 11, 12; \\ -\frac{1}{4}(S_8\sigma_yS_8^T + S_{10}\sigma_yS_{10}^T + S_{12}\sigma_yS_{12}^T)S_k, & k = 13, 14; \\ -\frac{1}{4}(S_8\sigma_yS_8^T + S_{10}\sigma_yS_{10}^T + S_{12}\sigma_yS_{12}^T + S_{14}\sigma_yS_{14}^T)S_k, & k \geq 15. \end{cases}$$

$$\frac{dS_k}{d\theta_x^3} = \quad (33)$$

$$\begin{cases} 0, & k \leq 16; \\ -\frac{1}{4}(S_{16}\sigma_yS_{16}^T)S_k, & k = 17, 18; \\ -\frac{1}{4}(S_{16}\sigma_yS_{16}^T + S_{18}\sigma_yS_{18}^T)S_k, & k = 19, 20; \\ -\frac{1}{4}(S_{16}\sigma_yS_{16}^T + S_{18}\sigma_yS_{18}^T + S_{20}\sigma_yS_{20}^T)S_k, & k = 21, 22; \\ -\frac{1}{4}(S_{16}\sigma_yS_{16}^T + S_{18}\sigma_yS_{18}^T + S_{20}\sigma_yS_{20}^T + S_{22}\sigma_yS_{22}^T)S_k, & k \geq 23. \end{cases}$$

Similarly, $$\frac{dS_k}{d\theta_y^1} = \begin{cases} 0, & k = 1; \\ \frac{1}{4}(S_1\sigma_xS_1^T)S_k, & k = 2, 3; \\ \frac{1}{4}(S_1\sigma_xS_1^T + S_3\sigma_xS_3^T)S_k, & k = 4, 5; \\ \frac{1}{4}(S_1\sigma_xS_1^T + S_3\sigma_xS_3^T + S_5\sigma_xS_5^T)S_k, & k = 6, 7; \\ \frac{1}{4}(S_1\sigma_xS_1^T + S_3\sigma_xS_3^T + S_5\sigma_xS_5^T + S_7\sigma_xS_7^T)S_k, & k \geq 8. \end{cases} \quad (34)$$

$$\frac{dS_k}{d\theta_y^2} = \quad (35)$$

$$\begin{cases} 0, & k \leq 9; \\ \frac{1}{4}(S_9\sigma_xS_9^T)S_k, & k = 10, 11; \\ \frac{1}{4}(S_9\sigma_xS_9^T + S_{11}\sigma_xS_{11}^T)S_k, & k = 12, 13; \\ \frac{1}{4}(S_9\sigma_xS_9^T + S_{11}\sigma_xS_{11}^T + S_{13}\sigma_xS_{13}^T)S_k, & k = 14, 15; \\ \frac{1}{4}(S_9\sigma_xS_9^T + S_{11}\sigma_xS_{11}^T + S_{13}\sigma_xS_{13}^T + S_{15}\sigma_xS_{15}^T)S_k, & k \geq 16. \end{cases}$$

$$\frac{dS_k}{d\theta_y^3} = \quad (36)$$

$$\begin{cases} 0, & k \leq 17; \\ \frac{1}{4}(S_{17}\sigma_xS_{17}^T)S_k, & k = 18, 19; \\ \frac{1}{4}(S_{17}\sigma_xS_{17}^T + S_{19}\sigma_xS_{19}^T)S_k, & k = 20, 21; \\ \frac{1}{4}(S_{17}\sigma_xS_{17}^T + S_{19}\sigma_xS_{19}^T + S_{21}\sigma_xS_{21}^T)S_k, & k = 22, 23; \\ \frac{1}{4}(S_{17}\sigma_xS_{17}^T + S_{19}\sigma_xS_{19}^T + S_{21}\sigma_xS_{21}^T + S_{23}\sigma_xS_{23}^T)S_k, & k \geq 24. \end{cases}$$

In this subsection, the Jacobian is derived.
Let $$T_J(k) = \prod_{j=k+1}^{N} T_{1w}(j) = T_{1w}(k+1) \times \ldots \times T_{1w}(N), \quad (37)$$

and denote its blocks as $$T_J(k) = \begin{bmatrix} R_k^J & 1_k^J \\ 0 & 1 \end{bmatrix}. \quad (38)$$

Recalling Eq. (19), we have $$\frac{dT_{cl}(N)}{d\theta_x^1} = \begin{bmatrix} \frac{dS_N}{d\theta_x^1} & \frac{d1_N}{d\theta_x^1} \\ 0 & 0 \end{bmatrix} \quad (39)$$

$$= \frac{dT_{1w}(1)}{d\theta_x^1} T_{1w}(2) \ldots T_{1w}(N) +$$

$$T_{1w}(1)T_{1w}(2)\frac{dT_{1w}(3)}{d\theta_x^1}T_{1w}(4) \ldots T_{1w}(N) +$$

$$T_{1w}(1)T_{1w}(2)T_{1w}(3)T_{1w}(4)\frac{dT_{1w}(5)}{d\theta_x^1}T_{1w}(6) \ldots T_{1w}(N) +$$

$$T_{1w}(1)T_{1w}(2)T_{1w}(3)T_{1w}(4)T_{1w}(5)T_{1w}(6)$$

$$\frac{dT_{1w}(7)}{d\theta_x^1}T_{1w}(8) \ldots T_{1w}(N)$$

$$= \begin{bmatrix} -R_1\frac{\sigma_y}{4} & 0 \\ 0 & 0 \end{bmatrix} T_J(1) + T_{cl}(2)\begin{bmatrix} -R_3\frac{\sigma_y}{4} & 0 \\ 0 & 0 \end{bmatrix} T_J(3) +$$

$$T_{cl}(4)\begin{bmatrix} -R_5\frac{\sigma_y}{4} & 0 \\ 0 & 0 \end{bmatrix} T_J(5) + T_{cl}(6)\begin{bmatrix} -R_7\frac{\sigma_y}{4} & 0 \\ 0 & 0 \end{bmatrix} T_J(7).$$

The last equality is obtained by the definition of $T_{cl}$ and $T_J$. Proceeding further, we have $$\frac{dT_{cl}(N)}{d\theta_x^1} = \begin{bmatrix} -R_1\frac{\sigma_y}{4} & 0 \\ 0 & 0 \end{bmatrix}\begin{bmatrix} R_1^J & 1_1^J \\ 0 & 1 \end{bmatrix} +$$

$$\begin{bmatrix} S_2 & 1_2 \\ 0 & 1 \end{bmatrix}\begin{bmatrix} -R_3\frac{\sigma_y}{4} & 0 \\ 0 & 0 \end{bmatrix}\begin{bmatrix} R_3^J & 1_3^J \\ 0 & 1 \end{bmatrix} +$$

$$\begin{bmatrix} S_4 & 1_4 \\ 0 & 1 \end{bmatrix}\begin{bmatrix} -R_5\frac{\sigma_y}{4} & 0 \\ 0 & 0 \end{bmatrix}\begin{bmatrix} R_5^J & 1_5^J \\ 0 & 1 \end{bmatrix} +$$

$$\begin{bmatrix} S_6 & 1_6 \\ 0 & 1 \end{bmatrix}\begin{bmatrix} -R_7\frac{\sigma_y}{4} & 0 \\ 0 & 0 \end{bmatrix}\begin{bmatrix} R_7^J & 1_7^J \\ 0 & 1 \end{bmatrix}$$

$$\begin{bmatrix} -S_1\frac{\sigma_y}{4}R_1^J - S_3\frac{\sigma_y}{4}R_3^J - S_5\frac{\sigma_y}{4}R_5^J - S_7\frac{\sigma_y}{4}R_7^J - \\ 0 \\ S_1\frac{\sigma_y}{4}1_1^J - S_3\frac{\sigma_y}{4}1_3^J - S_5\frac{\sigma_y}{4}1_5^J - S_7\frac{\sigma_y}{4}1_7^J \\ 0 \end{bmatrix}.$$

Therefore, the derivative of the position vector $1_N$ with respect to the joint angle $\theta_x^1$ is $$\frac{d1_N}{d\theta_x^1} = -S_1\frac{\sigma_y}{4}1_1^J - S_3\frac{\sigma_y}{4}1_3^J - S_5\frac{\sigma_y}{4}1_5^J - S_7\frac{\sigma_y}{4}1_7^J \quad (40)$$

$$= \frac{S_1}{4}\begin{bmatrix} -1_{1,3}^J \\ 0 \\ 1_{1,1}^J \end{bmatrix} + \frac{S_3}{4}\begin{bmatrix} -1_{3,3}^J \\ 0 \\ 1_{3,1}^J \end{bmatrix} + \frac{S_5}{4}\begin{bmatrix} -1_{5,3}^J \\ 0 \\ 1_{5,1}^J \end{bmatrix} + \frac{S_7}{4}\begin{bmatrix} -1_{7,3}^J \\ 0 \\ 1_{7,1}^J \end{bmatrix}.$$

In the above examples, the sequence of ordered locations and six-degrees of freedom were considered in configuring articulatable segments to remain within a boundary region, sometimes called a safe path. However, in some applications, consideration of only two-degrees of freedom may be sufficient. The x-y position could be controlled, or the pitch and the yaw could be controlled. In these applications, each waypoint only includes two degrees of freedom corresponding to an insertion depth and the above processes become less computationally intensive while the safe path is followed.

The above processes are applicable to a mode of endoscope operation in which the operator can directly articulate only the tip segment, e.g., segment 101-1, insertion causes new safe waypoints to be created along the path traced by the tip. The above techniques are used in configuring the trailing segments to follow the safe path.

In another mode of operation, the operator can make Cartesian commands at the tip and the rest of the segments make coordinated moves to accomplish that move within their respective safe regions, referred to as a boundary region above. The workspace at the tip is quite limited due to the safe region constraints, but a roll-only mode of operation would fall into this category of operation. In one aspect, the roll-only mode of operation could be achieved by simply commanding a roll at the tip subject to the safe region constraints as discussed above. However, an alternative approach for the roll-only mode of operation that utilizes bend angle and bend direction waypoints is described more completely below.

For example, a segment state that prevents articulation but allows roll to propagate from the base of the steerable medical device (proximal end) to the tip of the steerable medical device (distal end) may be desirable. In one aspect to propagate roll, annular joint limits are generated that prevent the combined bend angle of a segment from changing more than a few degrees, but allow individual joint angles (yaw and pitch) to vary. However, this alone does not force the shape of the steerable medical device to be maintained as articulatable segments can move independently within their respective annuli.

Ideally, when a pure roll is commanded, all the segments in steerable medical device 100 would maintain their shape and simply transmit proximal roll distally. As long as transmitting the proximal roll segment by segment does not change the shape of steerable medical device 100, steerable medical device 100 would remain within the boundary region. However, when a steerable medical device has articulatable segments with redundant degrees of freedom, the minimum joint velocity solution can change the shape of that medical device. In one aspect, a steerable medical device with more than two articulatable segments, insertion, and roll has redundant degrees of freedom.

In one aspect, the roll is transmitted distally while maintaining each articulatable segment within the boundary region by determining changes in joint angles due to roll on a per-segment basis, which ensures that the shape of each articulatable segment is maintained and so each articulatable segment follows the safe path. When each of the articulatable segments has been rolled, a final iteration can done to correct any deviation in the position and orientation of the tip.

Figure 6:
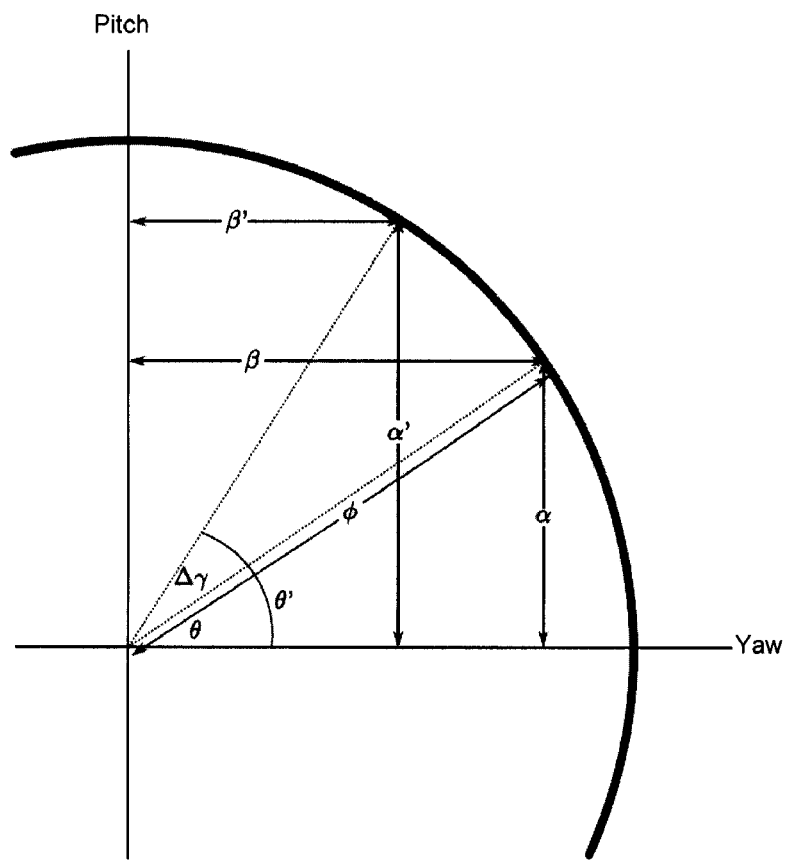
FIG. 6 is an illustration of an approximate change in joint angles due to roll.

FIG. 6 is an illustration of one method to approximate changes in segment joint angles as roll is propagated on a per segment basis. In this method, when the base of a segment rolls though an angle $-\Delta\gamma$, new pitch angle $\alpha'$ and new yaw angle $\beta'$ are generated for that segment by maintaining approximate bend angle $\phi$ and direction $\theta$. From FIG. 6, for a current pitch angle $\alpha$ and a current yaw angle $\beta$, approximate bend angle $\phi$ is defined as, $$\phi = \sqrt{\alpha^2 + \beta^2}$$

while direction $\theta$ is defined as, $$\theta = \arctan(\alpha/\beta)$$

and new direction θ' is $$\theta' = \theta + \Delta\gamma.$$

With these definitions, new pitch angle α' and new yaw angle β' are $$\alpha' = \phi * \sin(\theta')$$

$$\beta' = \phi * \cos(\theta').$$

New pitch angle α' and new yaw angle β' for the segment are implemented, in one aspect, by assuming equal joint angles for the yaw joints and equal angles for the pitch joints in the segment.

Thus, this method takes an initial roll −Δγ, current pitch angle α and current yaw angle β for each segment and propagates that roll segment by segment from the proximal end to the distal end of steerable medical device 100. This method of decoupling the segments and determining the roll segment by segment without feedback is useful when there is more than one pair of yaw and pitch joints in a segment.

An alternative to the above approach without feedback is to perform an iterative solution on a segment by segment basis to transmit the roll distally from the base of the medical device while maintaining the current shape of each segment. The iterative analysis is performed until convergence is reached on a per-segment basis, i.e., a segment is iterated on until converged and then the next segment is processed.

Figure 7:
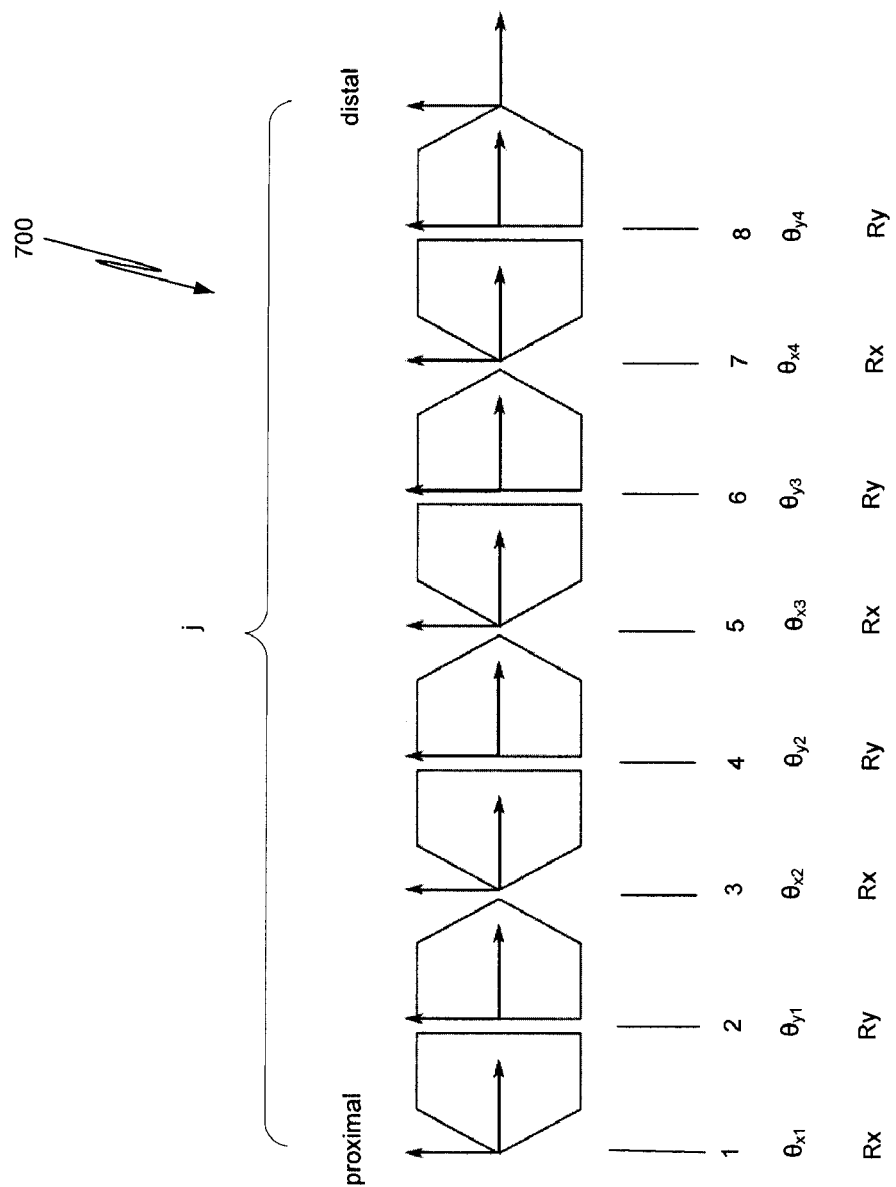
FIG. 7 is a diagrammatic view of elements of a kinematic model that can be used in the method of FIG. 8.

A kinematic model of a segment is used in this iterative solution. FIG. 7 is a diagrammatic drawing of a general kinematic model 700 for a representative segment j of steerable endoscope 100 with an indication of the joint angle and the appropriate roll matrix. Here, j is an integer ranging from one to the number of articulatable segments. In determining the orientation of each of the links, a transform is defined for each link.

The transform for the pitch-links is:

$$T_{xi} = \begin{bmatrix} R_x(\theta_{xi}) & \begin{pmatrix} 0 \\ 0 \\ -a(x_i) \end{pmatrix} \\ 0 & 1 \end{bmatrix},$$

$i = 1$ to $4$ $a(x_i)$ is the displacement for link $x_i$; and $$R_x(\theta_{xi}) = \begin{bmatrix} 1 & 0 & 0 \\ 0 & \cos(\theta_{xi}) & -\sin(\theta_{xi}) \\ 0 & \sin(\theta_{xi}) & \cos(\theta_{xi}) \end{bmatrix}$$

The transform for the yaw-links is:

$$T_{yi} = \begin{bmatrix} R_y(-\theta_{yi}) & \begin{pmatrix} 0 \\ 0 \\ -a(y_i) \end{pmatrix} \\ 0 & 1 \end{bmatrix},$$

$i = 1$ to $4$ $a(y_i)$ is the displacement for link yi $$R_y(-\theta_{yi}) = \begin{bmatrix} \cos(\theta_{yi}) & 0 & -\sin(\theta_{yi}) \\ 0 & 1 & 0 \\ \sin(\theta_{yi}) & 0 & \cos(\theta_{yi}) \end{bmatrix}$$

Note that the rotations in kinematic model 700 are defined differently than those in kinematic model 500 above.

In this aspect, as noted above, only the yaw and pitch are of interest in determining the orientation. Thus, the iterative solution is obtained using the roll matrices $R_x$ and $R_y$, e.g., three rows corresponding to the orientation and three columns corresponding to pitch, yaw, and a virtual roll at the distal end of the segment. The virtual roll should be equal to the base roll at the proximal end of the segment, because this kinematic model does not allow roll along the segment.

In the approach that used kinematic model 700, orientation data was utilized to transmit roll distally. In another aspect, x-y position data with a kinematic model could be used to maintain the shape of steerable medical device on a segment by segment basis for a displacement in the z-direction. Utilizing, both position and orientation data at the same time over-constrains the determination.

Figure 8:
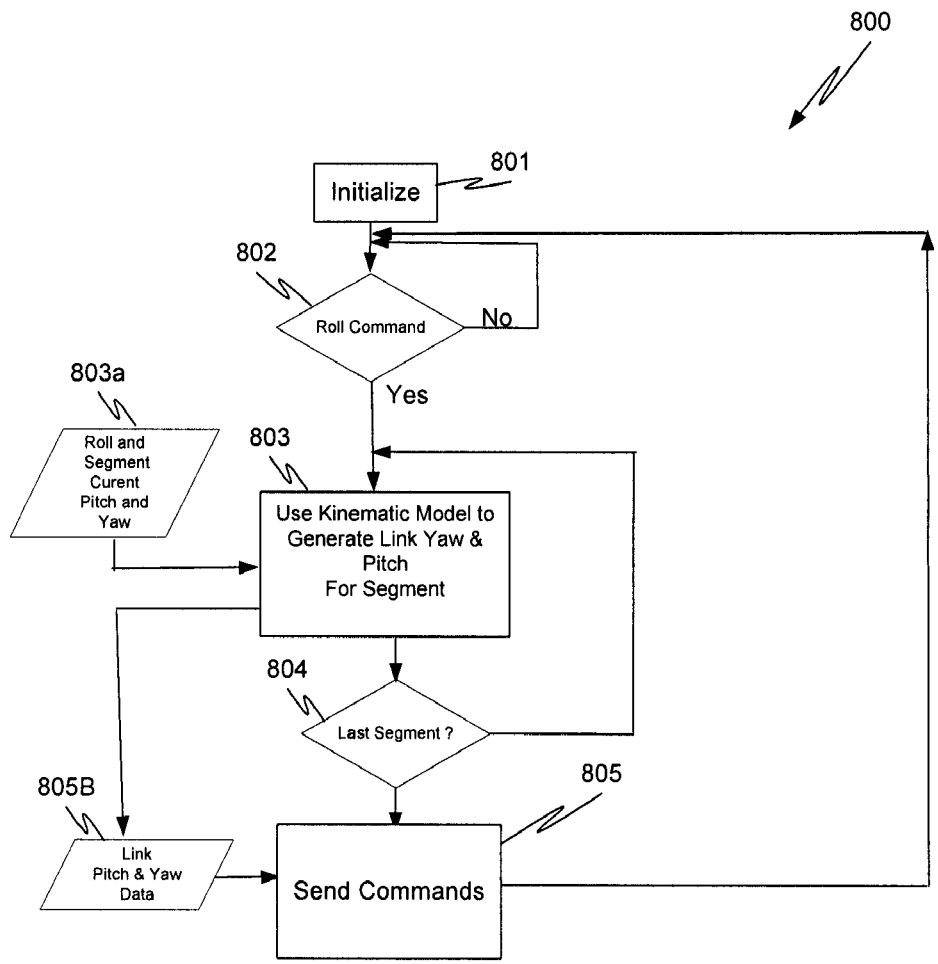
FIG. 8 is a process flow diagram for one embodiment of a method transferring roll distally in a medical device with articulatable segments.

FIG. 8 is a process flow diagram of one embodiment of a process 800 for transmitting proximal roll to a tip of steerable endoscope 100. In one aspect, instructions in a METHOD 800 module 933 in memory 230A of system controller 220A (FIG. 9) are executed on a processor in processor module 250 to perform at least some of the operations described more completely below.

Upon initiation of method 800, an INITIALIZE operation 801 is performed. INITIALIZE operation 801 initializes any variables, memory structures etc. that are need for subsequent operations in method 800. Upon completion INITIALIZE operation 801 transfers processing to ROLL COMMAND check operation 802.

Processing remains in ROLL COMMAND check operation 802 until a roll command is received from the operator of steerable endoscope 100. Upon receiving a roll command, ROLL COMMAND check operation 802 transfers processing to USE KINEMATIC MODEL TO GENERATE LINK YAW AND PITCH FOR SEGMENT process 803. Check operation 802 should not be interpreted as requiring polling. Check operation 802, for example, could be implemented as part of an event handler and when a roll command event occurs, process 803 is launched.

USE KINEMATIC MODEL TO GENERATE LINK YAW AND PITCH FOR SEGMENT process 803 retrieves the current yaw and pitch for each articulatable segment from ROLL AND SEGMENT CURRENT PITCH AND YAW data 803A for use in kinematic model 700 (FIG. 7). Starting with the most proximal articulatable segment, the desired orientation for that segment is set equal to the original orientation. The base of the segment, e.g., the most proximal portion of the segment, is rotated by the amount of the commanded roll around the x-axis of the segment base.

In one aspect, the kinematic model is seeded with an approximate solution, such as that generated using FIG. 6, to reduce the number of iterations required for convergence. When the analysis for a segment is completed, yaw data and pitch data are available for each link in that segment.

Upon completion of processing the segment, process 803 transfers to LAST SEGMENT CHECK operation 804. LAST SEGMENT CHECK operation 804 determines whether all the segments have been processed by the kinematic model. If the necessary segments have been processed, check operation 804 transfers to SEND COMMAND operation 805 and otherwise returns to process 803.

When the configuration for each of the articulatable segments is determined, LAST SEGMENT check operation 804 transfers processing to SEND COMMAND operation 805. In SEND COMMAND operation 805, the processor in processor module 250 (FIG. 9) sends the at least one command to the motors in endoscope controller 240 to configure the articulatable segments based upon the yaw and pitch orientations generated in process 803. In response to the command or commands, endoscope controller 240 configures the articulatable segments so that as these segments roll, the segments are constrained to stay within the boundary region.

The resulting configuration of the articulatable segments maintains the shape of endoscope 100 while the proximal roll is transmitted distally. Method 800 assures that steerable endoscope 100 stays within the boundary region discussed above as the proximal roll is transmitted.

Figure 9:
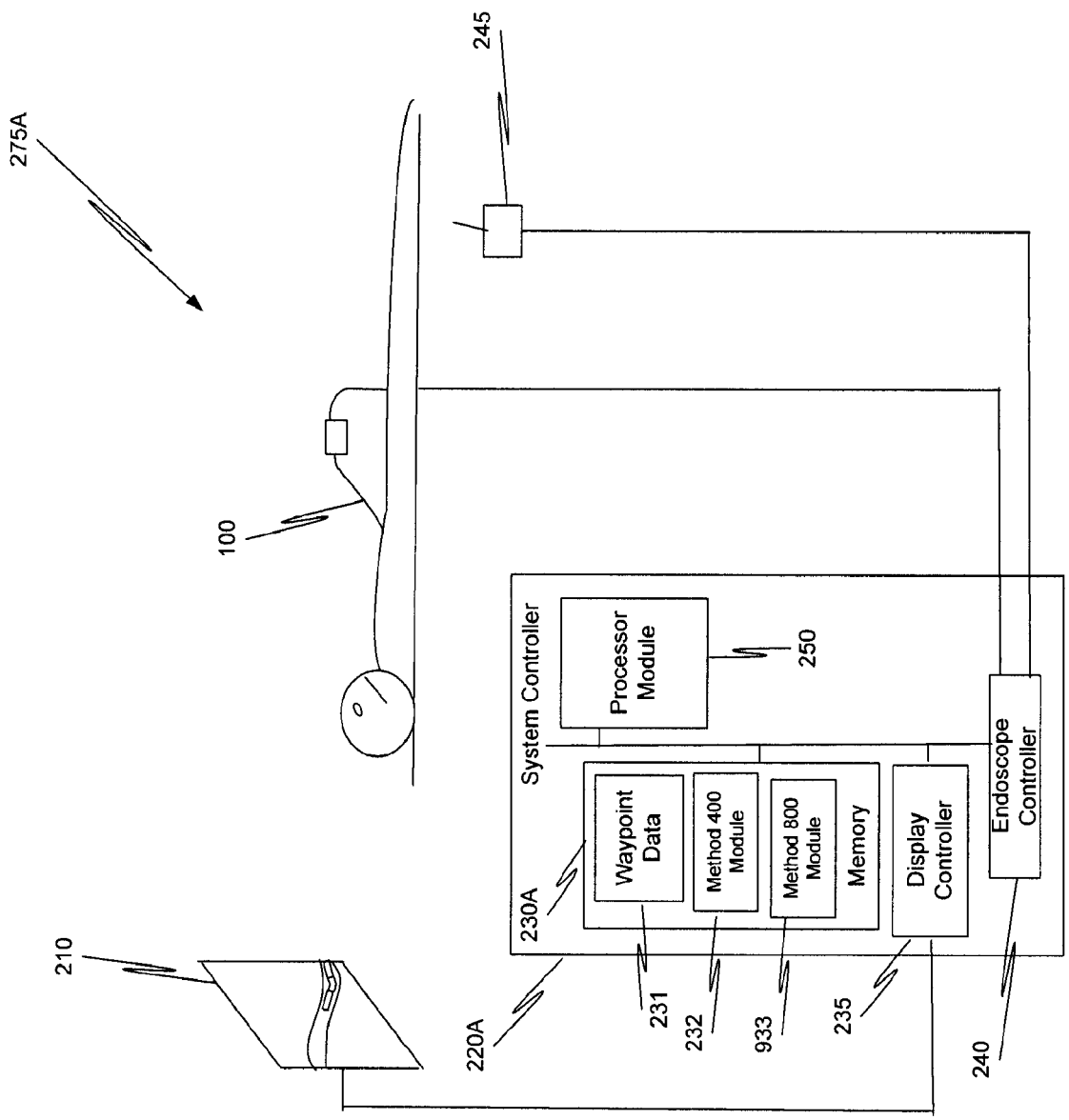
FIG. 9 is a diagrammatic view of another apparatus used in one aspect of the processes and operations described herein.

In FIG. 9, elements with the same reference numeral as elements in FIG. 2 are the same or equivalent elements. Accordingly, the description of those elements with respect to FIG. 2 is incorporated herein by reference for FIG. 9.

System controller 220 (FIG. 2) and system controller 220A (FIG. 9) are illustrated as unified structures for ease of illustration and understanding. This is illustrative only and is not intended to be limiting. The various component of system controllers 220 and 220A can be located apart and still perform the functions described.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes include various special device positions and orientations.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

The term "flexible" in association with a mechanical structure or component should be broadly construed. In essence, it means the structure or component can be bent without harm. For example, a flexible mechanical structure may include a series of closely spaced components that are similar to "vertebrae" in a snake-like arrangement. In such an arrangement, each component is a short link in a kinematic chain, and movable mechanical constraints (e.g., pin hinge, cup and ball, and the like) between each link may allow one (e.g., pitch) or two (e.g., pitch and yaw) degrees of freedom (DOF) of relative movement between the links. As another example, a flexible mechanical structure may be continuous, such as a closed bendable tube (e.g., nitinol, polymer, and the like) or other bendable piece (e.g., kerf-cut tube, helical coil, and the like). Accordingly, a short, flexible structure may serve as, and be modeled as, a single mechanical constraint (joint) providing one or more DOFs between two links in a kinematic chain, even though the structure itself may be a kinematic chain made of several coupled links.

While the memory in FIGS. 2 and 9 is illustrated as a unified structure, this should not be interpreted as requiring that all memory is at the same physical location. All or part of the memory can be in a different physical location than a processor. Memory refers to a volatile memory, a non-volatile memory, or any combination of the two.

A processor is coupled to a memory containing instructions executed by the processor. This could be accomplished within a computer system, or alternatively via a connection to another computer via modems and analog lines, or digital interfaces and a digital carrier line.

Herein, a computer program product comprises a medium configured to store computer readable code needed for any one or any combination of the operations described with respect to module 232, module 933 or in which computer readable code for any one or any combination of operations described with respect to modules 232 and 933 is stored. Some examples of computer program products are CD-ROM discs, DVD discs, flash memory, ROM cards, floppy discs, magnetic tapes, computer hard drives, servers on a network and signals transmitted over a network representing computer readable program code. A tangible computer program product comprises a tangible medium configured to store computer readable instructions for any one of, or any combination of operations described with respect to modules 232 and 933 or in which computer readable instructions for any one of, or any combination of operations described with respect to modules 232 and 933 are stored. Tangible computer program products are CD-ROM discs, DVD discs, flash memory, ROM cards, floppy discs, magnetic tapes, computer hard drives and other physical storage mediums.

In view of this disclosure, instructions used in any one of, or any combination of operations described with respect to modules 232 and 933 can be implemented in a wide variety of computer system configurations using an operating system and computer programming language of interest to the user.

All examples and illustrative references are non-limiting and should not be used to limit the claims to specific implementations and embodiments described herein and their equivalents. The headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

We claim:

1. A method comprising:
storing, by a controller, waypoints of a steerable medical device, the waypoints being locations of the steerable medical device within a patient as the medical device is moved within the patient, the waypoints being determined as the steerable medical device is moved towards a desired location within the patient, wherein said stored waypoints comprise an ordered sequence of locations, and further wherein said ordered sequence of locations defines a safe path for moving an articulatable portion of said steerable medical device within the patient, the articulatable portion of the steerable medical device comprising one or more segments, each of the one or more segments comprising a plurality of links, adjacent links of the plurality of links being connected by a joint; and
constraining, by the controller as the articulatable portion of the steerable medical devices is moved within the patient, the articulatable portion of the steerable medical device to remain within a boundary region enclosing the safe path as the articulatable portion of the steerable medical device follows the safe path, the boundary region being based on the waypoints,
wherein a link in the articulatable segment deviating from the safe path remains within the boundary region,
wherein the constraining comprises:
generating position and orientation data for each of the one or more segments of the articulatable portion using the ordered sequence of locations and a kinematic model of the articulatable portion of the steerable medical device; and
wherein said generating further comprises:
minimizing a cost function associated with the kinematic model to generate said position and orientation data for each of said one or more segments; and
wherein said minimizing a cost function further comprises:
minimizing the sum of the absolute values of relative joint angles, with an additional constraint that link positions not deviate by more than a distance $\Delta$ at each of the waypoints in said ordered sequence of locations.

2. The method of claim 1, the constraining further comprising:
sending, by the controller, at least one command to a controller of the steerable medical device to constrain the links of said articulatable portion of said steerable medical device within the boundary region.

3. The method of claim 1, wherein said boundary region comprises a tube having a cross-section.

4. The method of claim 3, wherein said cross-section comprises one of a circular cross-section, an oblate cross-section, and a rectangular-cross-section.

5. The method of claim 1, wherein storing the waypoint further comprises:
determining a location of a tip of the steerable medical device; and
saving the location of the tip of the steerable medical device as a waypoint if a link of the steerable medical device is inserted into the patient following the determining.

6. The method of claim 1, further comprising:
determining whether a tip of a steerable medical device is being withdrawn from the patient; and
deleting a saved waypoint if the determining finds that a link of the steerable medical device is withdrawn from patient.

* * * * *